(12) United States Patent
Balooch et al.

(10) Patent No.: US 10,716,391 B2
(45) Date of Patent: Jul. 21, 2020

(54) CONNECTED HAIRBRUSH

(71) Applicant: L'OREAL, Paris (FR)

(72) Inventors: Guive Balooch, Clark, NJ (US);
Gregoire Charraud, Colombes (FR);
Michael Haddad, Paris (FR); Helga Malaprade, Vincennes (FR);
Jean-Loup Loyer, Paris (FR)

(73) Assignee: L'OREAL, Paris (FR)

( * ) Notice: Subject to any disclaimer, the term of this patent is extended or adjusted under 35 U.S.C. 154(b) by 225 days.

(21) Appl. No.: 15/856,936

(22) Filed: Dec. 28, 2017

(65) Prior Publication Data

US 2018/0184796 A1    Jul. 5, 2018

Related U.S. Application Data

(60) Provisional application No. 62/440,488, filed on Dec. 30, 2016.

(51) Int. Cl.
| | |
|---|---|
| A46B 15/00 | (2006.01) |
| A46B 9/02 | (2006.01) |
| A45D 24/10 | (2006.01) |
| G09B 19/00 | (2006.01) |
| A45D 44/00 | (2006.01) |

(Continued)

(52) U.S. Cl.
CPC ......... *A46B 15/0002* (2013.01); *A45D 24/10* (2013.01); *A45D 44/005* (2013.01); *A46B 9/023* (2013.01); *A46B 15/0006* (2013.01); *A46B 15/0038* (2013.01); *A61B 5/1032* (2013.01); *A61B 5/448* (2013.01); *G09B 19/003* (2013.01); *G09B 19/0076* (2013.01);

*G09B 19/24* (2013.01); *A45D 2044/007* (2013.01); *A46B 2200/104* (2013.01); *G09B 5/02* (2013.01); *G09B 5/04* (2013.01)

(58) Field of Classification Search
None
See application file for complete search history.

(56) References Cited

U.S. PATENT DOCUMENTS

| | | | | |
|---|---|---|---|---|
| 4,167,869 A | * | 9/1979 | Gikas | A45D 24/10 132/219 |
| 2010/0304339 A1 | * | 12/2010 | Soto | G09B 19/0076 434/94 |

(Continued)

FOREIGN PATENT DOCUMENTS

FR    2 964 023 A1    3/2012

OTHER PUBLICATIONS

International Search Report and Written Opinion dated Mar. 16, 2018 in PCT/US2017/068774, 18 pages.

(Continued)

*Primary Examiner* — Jason T Yen
(74) *Attorney, Agent, or Firm* — Oblon, McClelland, Maier & Neustadt, L.L.P.

(57) ABSTRACT

A system that includes a styling tool configured to treat or shape a user's hair; and a client device configured to communicate with the styling tool and provide feedback to the user regarding a user's usage of the styling tool based at least in part on measured data captured by the styling tool. The styling tool may be a hairbrush that includes circuitry and/or sensors configured to detect one or more of sound, acceleration, force, rotation, hair humidity, and ambient temperature and humidity.

6 Claims, 6 Drawing Sheets

(51) Int. Cl.
*G09B 19/24* (2006.01)
*A61B 5/103* (2006.01)
*A61B 5/00* (2006.01)
*G09B 5/04* (2006.01)
*G09B 5/02* (2006.01)

(56) References Cited

U.S. PATENT DOCUMENTS

| | | | | |
|---|---|---|---|---|
| 2011/0047046 | A1* | 2/2011 | Torres | G06Q 30/0613 |
| | | | | 705/26.41 |
| 2011/0289015 | A1* | 11/2011 | Mei | G06Q 10/04 |
| | | | | 705/347 |
| 2015/0342515 | A1* | 12/2015 | Hutchings | A46B 9/023 |
| | | | | 132/200 |
| 2016/0140986 | A1* | 5/2016 | Bowers | A61B 3/113 |
| | | | | 704/271 |
| 2016/0278690 | A1* | 9/2016 | Hyde | A46B 15/0055 |

OTHER PUBLICATIONS

European Office Action dated Jun. 3, 2019 in European Patent Application No. 17835771.1, 3 pages.

* cited by examiner

CONNECTED HAIRBRUSH

CROSS-REFERENCE TO RELATED APPLICATIONS

The present application is related to and claims the benefit of U.S. Provisional Application No. 62/440,488, filed Dec. 30, 2016, the entire contents of which is hereby incorporated herein by reference.

BACKGROUND

A hairbrush that transmits sensed data to a remote entity is disclosed by U.S. Publication No. 2015/0342515A1, which is herein incorporated by reference. However, there is a need for a connected hairbrush that provides improved hair health and brushing gesture indicators, user live feedback, a learning protocol, personalized hair care recommendations, bristles/teeth/cushion designed to output sound carrying valuable information at any wavelength of interest and an improved method of evaluating the state of the user's hair surface with a brush/comb.

SUMMARY

In an embodiment, a connected hair brush provides to the end consumer hair health information and brushing motion coaching by recording day-to day brushing sessions.

The internal circuitry of the hair brush measures sound, acceleration, force, rotation, hair humidity, ambient temperature and humidity. The obtained raw signals are remotely processed on a cloud architecture by algorithms enabling analytic consolidation over lifetime.

The end consumer's benefits are to monitor changes over time, get personalized advice and product routine recommendation.

The following objectives are achieved with the present embodiments:

1) Based on a signal measurement the internal circuitry of the hair brush triggers an haptic feedback to the end consumer to warn her/him and modify the motion. For ex. pressing too hard might sensitize the scalp, using too much force during session might damage the hair fiber, etc.
2) Based on hair tangled measurements detected by the internal circuitry the triggered haptic feedback can help to untangle the hair while brushing.
3) Day to day sound measurements processed by algorithms (relative energy comparison and frequency analysis) on the cloud architecture can predict when a shampoo and conditioners are no longer having effect and alert the end consumer to re-apply hair treatment or to obtain a certain type of shampoo, conditioner, or other product.
4) The number of brushing strokes can be counted and the stroke rate on fixed period of time can show relative tangling rate.
5) Relative hair-surface damage can be assessed by cloud algorithm thanks to a frequency analysis of the sound generated by the hair resonance contact with the boar and plastic bristles.
6) The consolidation of different signals can provide different hair/scalp health scores such as:
    a. Hair brushing motion coach: accelerometer+force+gyroscope
    b. Scalp sensitization: force+gyroscope+sound
    c. Untangling score: force+accelerometer+gyroscope+sound
    d. Stroke count: sound+accelerometer
7) The connected app interface displays hair health information, coaching and product routine information related to hair analysis and environment data.
8) The contact pin that measures if the hair is wet or dry can help cloud algorithms to determine the hair damage, vulnerability and adjust dynamically the algorithms thresholds
9) The accuracy of the hair damage algorithm can be dynamically adjusted thanks to the declared curliness degree.

The following solutions can be implemented to achieve the objectives:

Microphone Frequency and sound energy to analyze hair damage.

Load cells to detect force applied between head and handle for brushing gesture analysis.

Accelerometer/Gyroscope Number of hair brushing strokes.

Conducted pin Quills to detect if hair is wet or dry.

Haptic feedback For user hair brush motion feedback.

Wi-Fi & Bluetooth To connect to the cloud and the app.

Ambient temperature/humidity to make algorithms independent to ambient conditions (normalize measurements algorithms).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
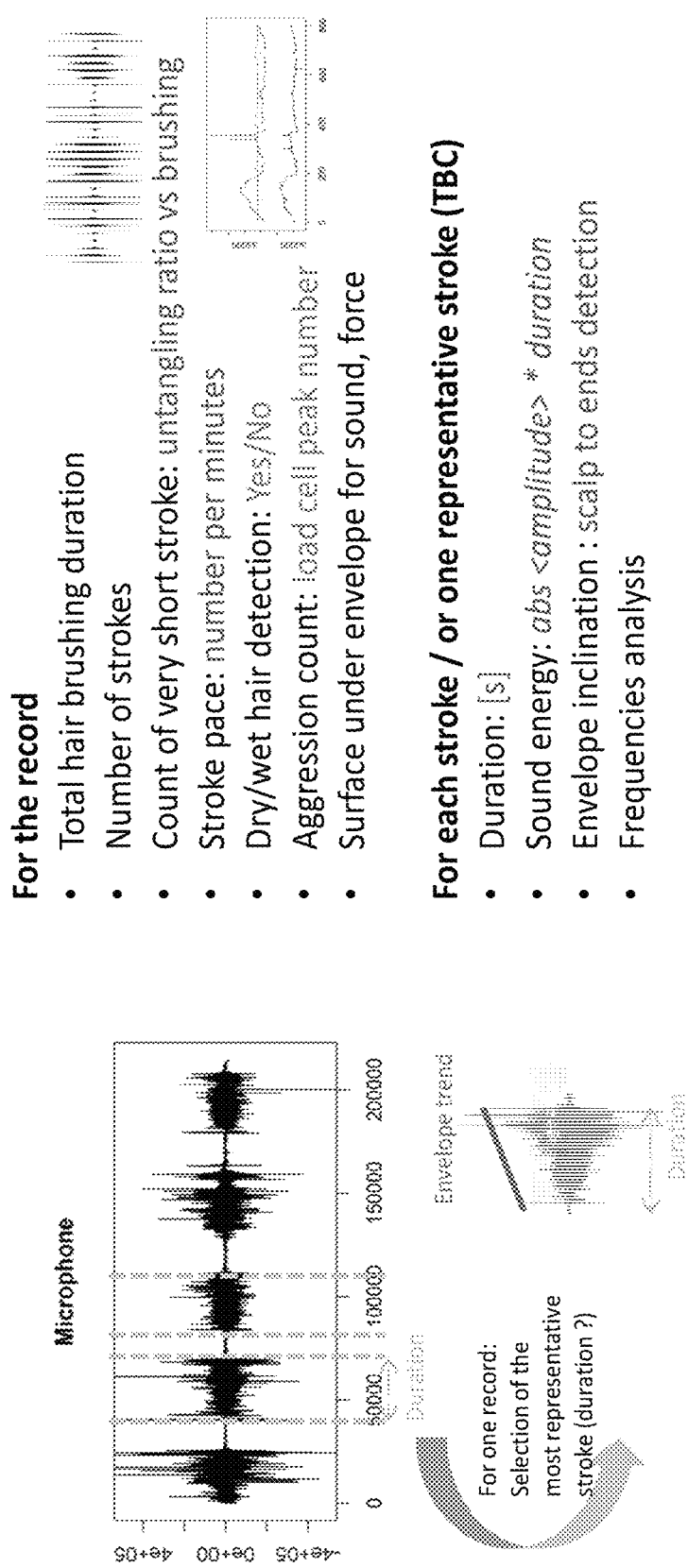
FIG. 1 depicts a signal processing example according to an embodiment.

The present embodiments are directed to a smart, connected hairbrush, comb, or toothbrush that provides improved hair health and brushing gesture indicators, user live feedback, a learning protocol, personalized hair care recommendations, bristles/teeth/cushion designed to output sound carrying valuable information at any wavelength of interest, and an improved method of evaluating the state of the user's hair surface with a brush/comb. First an overview of the features of the present embodiments will be described, followed by a description of a device, system, and method according to the embodiments.

I. Hair Health and Brushing Gesture Indicators

A connected hairstyling tool that captures raw data thanks to embedded sensors is able to determine hair attributes and brushing gesture indicators thanks to data information analysis processed locally or remotely. All indicators might be computed partially or totally by a questionnaire filled by auto assessment or third party evaluation. The questionnaire may be directed towards targeting the user's hair surface state based on age and habits of a damaging process. However, regarding brushing gesture analysis there are several indicators that can be followed by the end user and/or hairstylist such as: number of strokes per session, number of strokes of brushing versus number of untangling gestures. The stroke pace is also an indicator of gesture. At the end of a brushing session, an expert evaluator may also count the number of hairs remaining in the brush as more hair in the brush indicates that the user has more fragile hair and this potentially indicates that a force applied by the hairbrush might be too strong. Sensor signals may be combined so as to consolidate hair indicators and dynamically weight/adjust thresholds and outputs. Raw signals can be analyzed point-by-point or aggregated over a part or total duration of the brushing session. These indicators comprise:
1. Hair health as combination of a few or all of
Hair damage surface state based on sound analysis (including but not limited to spectrum analysis, amplitude, energy and their combination) due to hair friction while going through bristles/teeth/cushion of the hairstyling tool.
Hair breakage based of force measurement and gesture analysis thanks 3 axis accelerometer and gyroscope linked to a hair damage assessment
Tangling degree based on sound analysis (spectral and energy but not limited to) during stroke motion and/or force measurement and/or accelerometer and gyroscope.
Dryness assessment based on day to day energy and spectral sound variation to determine when to reapply hair care product.
Hair moisture level to differentiate physical hair characteristic when wet or dry, as measured by humidity sensor.
Brushing index as combination of a few or all of
Brushing force energy integrated during a brushing session
Brushing stroke pace based on frequency of stroke motion and the duration of each stroke
Behavior monitoring gentle/aggressive gesture based on force measurement and motion analysis relying on a 3-axis accelerometer and gyro and/or computer vision via a camera and/or a magnetometer
Tangling snag count based on counting force peaks between handle and head including accelerometer and gyro and/or sound analysis.

All of these indicators will be displayed to the end user in the app/website/any digital medium. FIG. 1 shows a signal processing example according to this feature.

II. User Live Feedback

A connected hairstyling tool that captures raw data thanks to embedded sensors is able to coach over time and dynamically or not the end user to improve his hair health and brushing habit by taking in account environmental information. All feedback might be computed partially or totally by a questionnaire filled by auto assessment or third party evaluation. Sensors signals and external data may be combined so as to refine the feedback and advices over time. These feedbacks can be synchronized with brushing session or delivered asynchronously. Feedback can be delivered as vibration, light, sound, voice and displayed on app/website/computer/any digital medium. The feedback includes:
1. Improper brushing detection—Based on a force sensor (such as a 3-axis load cell between the handle and the head of the brush which measures the force applied by the hand on the brush while brushing, and also flexion force), 3 axis accelerometers, gyroscope, sound, the hairstyling tool will notify (through vibration, light, sound) the user that his brushing out of the recommended gesture/force/stroke number. These thresholds are adjusted based on his profile over time.
2. Reapply hair treatment—Based on day to day energy and spectral sound variation the user will be notified on app screen/email/website that he needs to reapply hair care treatment.
3. Weather alert—Based on localized weather on the ground information the user can be informed by notification of the impact of weather conditions on hair. The weather information includes temperature, humidity, wind, UV index, pollution and can be combined in hair metrics.
4. Hair care routine alert—Based on event time stamping, whether the user has a hairdresser appointment or coloration date, the app of the connected styling tool can remind the user when to reapply a hair care routine or make an appointment.
5. Personalized coaching—Over the time, based on hair profile clustering of the user, the app or website can provide to an identified user personalized advices and objectives as stroke number per session, dedicated product routine, gesture coaching, visual diagnosis that can be performed thanks to a photo (such as a "selfie" image) captured by a camera.

III. Learning Protocol

A connected hairstyling tool that captures raw data thanks to embedded sensors will be linked to a remote IT infrastructure able to store, process users data over time. Users can be clustered thanks to their characteristics and indicators computed after each brushing session and app usage. For one user, thresholds and results will be estimated and used ad input of comprising learning protocol:
1. Statistical clustering of user to qualify their score
Database collection of results and hair indicators mentioned in slide #4 will be analyzed to find statistical figures and number helping to qualify hair indicators result compared to the panel users.
Clusters and group can be determined on one or several parameters as brushing gesture, hair characteristics or business follow up.
Qualification of user group will help to display end user metrics in a user friendly way as "optimal, average, bad".
2. Learning process to predict hair condition
All hair information collected may be used as input of learning algorithms including diagnosis of hair condition auto assessed, the indicators and raw signals, business figures so as to predict hair condition over time among users.
The purpose is to evaluate automatically one or several following items:

Hair characteristics: such as length, hair diameter, curl level, nutrition, damage, manageability Brushing gesture: ideal brushing stroke number depending on hair length/curl, ideal force and gesture type Environment: "predict brushing duration based on weather condition frizzing hair for example"

Figure 2:
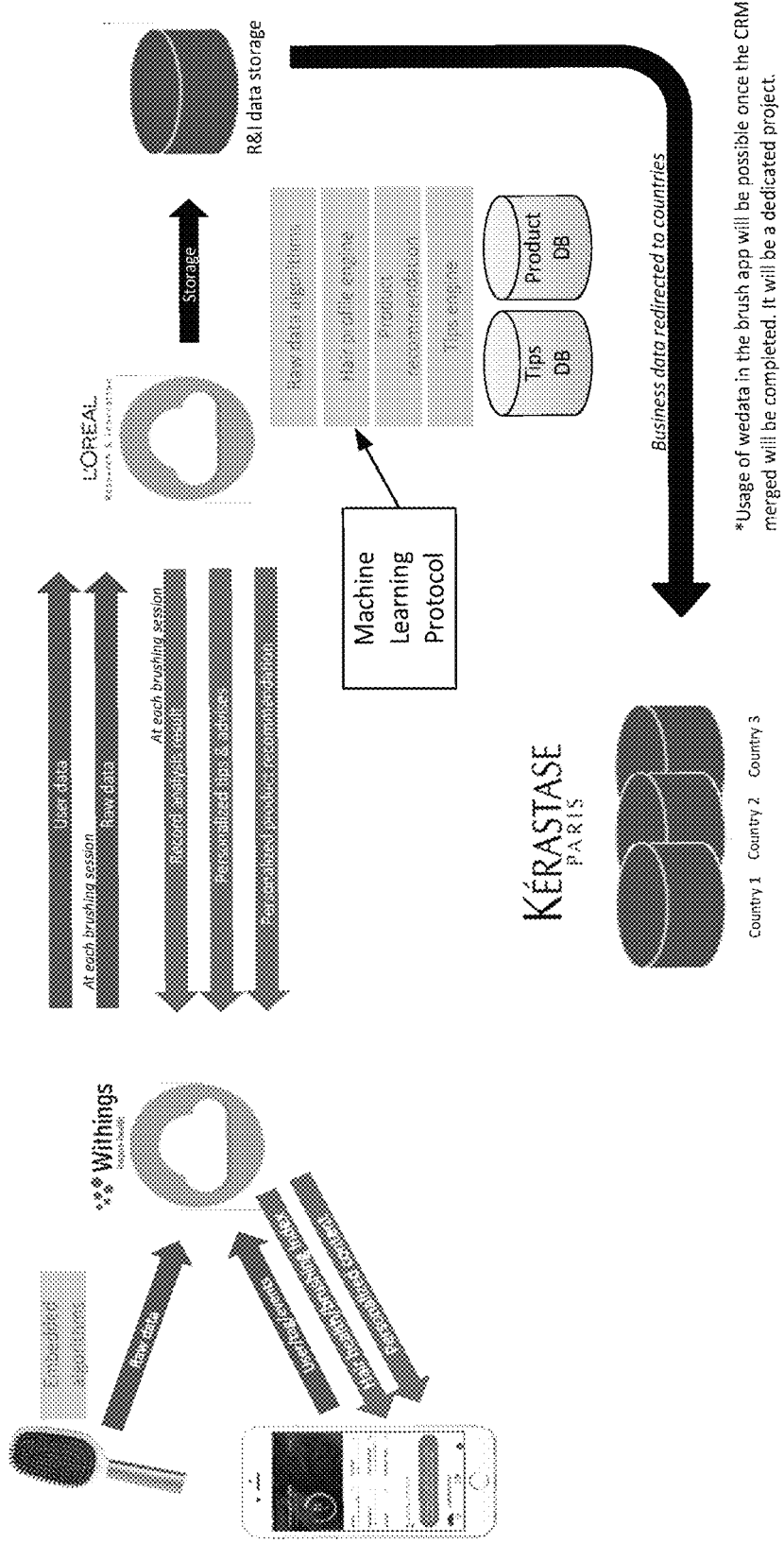
FIG. 2 depicts an IT infrastructure and dataflow from where a learning protocol can start.

FIG. 2 shows an example of an IT cloud infrastructure of a system which implements the above-noted concepts.

IV. Personalized Hair Care Recommendations

Figure 3:
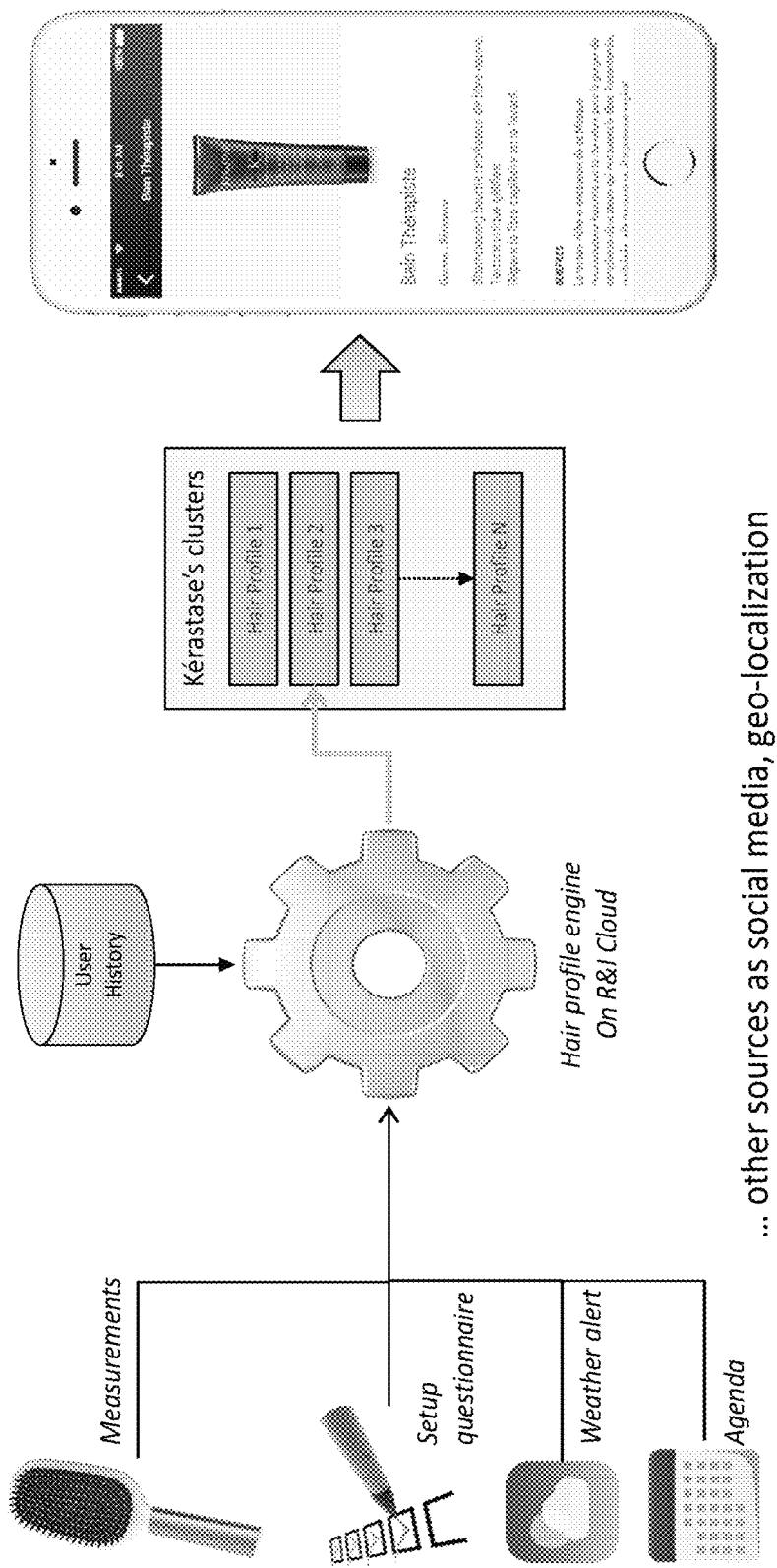
FIG. 3 depicts a system and method of providing product/service recommendations according to an embodiment.

A connected hairstyling tool that captures raw data thanks to embedded sensors and linked to external data information sources (weather, social networks, emails, business database, CRM, user agenda, geo-localization, calendar . . . ) can be aggregated to enable a personalized hair care routine and/or product recommendation and/or services (hairstylist). These recommendations can be displayed on email/app/computer/website as depicted in FIG. 3.

V. Bristles/Teeth/Cushion Designed to Sound

Measuring hair surface state with a microphone in a styling tool requires amplifying (resonance) frequencies due to hair frictions against material of the hairstyling tool and minimize contribution from non-relevant sources. Targeted frequencies or sound effect can be generated by designing on purpose specific cushion and or bristles and or teeth and or their mechanical integration. This design will determine the results obtained by applying some rules as:

Type of bristles: diameter, material (synthetic or/and animals hair like boar), length, elasticity, thickness.
Pattern of bristles/teeth: density, geometrical shape.
Position of the microphone on the styling tool.
Texture/material of cushion and mechanical enclosure.
Geometrical dimensions

VI. Additional Method to Evaluate Hair State Surface with a Brush/Comb

A system and/or hairbrush according to the present embodiments may further include a tribometer or an optical device apart from a camera (spectrometer, etc) to evaluate the state of the user's hair.

VII. Embodiment Description

A system according to an embodiment connects a hairbrush (as an example, but also could be a comb or toothbrush) with a client device. The client device receives inputs on the user's brushing gestures, provides feedback on hair health, and can correct the user's technique while using the hairbrush.

Figure 4A:
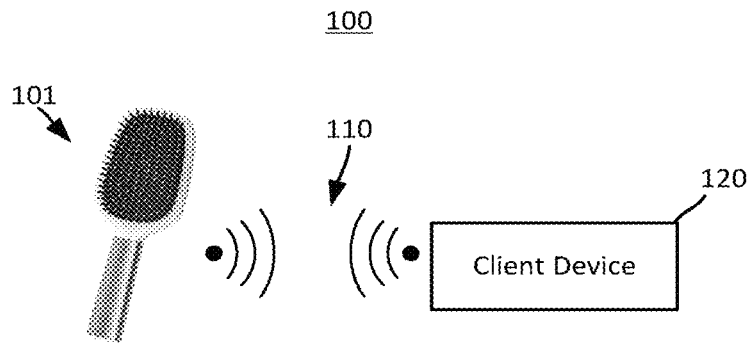
FIG. 4A depicts a system according to an embodiment that includes a hairbrush and a client device.

FIG. 4A shows a system 100 that includes a hairbrush 101 and a client device 120. It is noted that while element 101 is depicted as a hairbrush, it may also be a comb, a toothbrush, or a similar tool. In an embodiment, the hairbrush 101 is in communication with the client device 120 with a wireless signal 110. In an embodiment, the client device 120 is configured to operate a software application or set of software modules to receive and send communications from and to the hairbrush 101. In an example, the software application can send a protocol or target profile to the hairbrush 101, as well as receive data from the styling tool 101 to track the usage in real time.

Figure 4B:
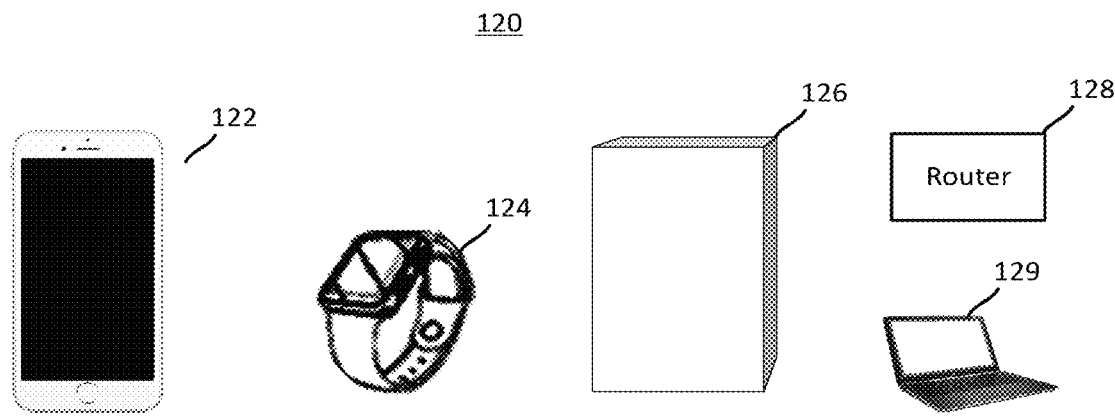
FIG. 4B depicts examples of client devices according to embodiments.

FIG. 4B shows different examples of the client devices 120 including, a mobile device 122, a wearable electronic 124, a television or magic mirror 126, a network router 128, and a personal computer 129.

The wireless signal 110 can be any appropriate signal such as an electromagnetic signal including WIFI, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 4C:
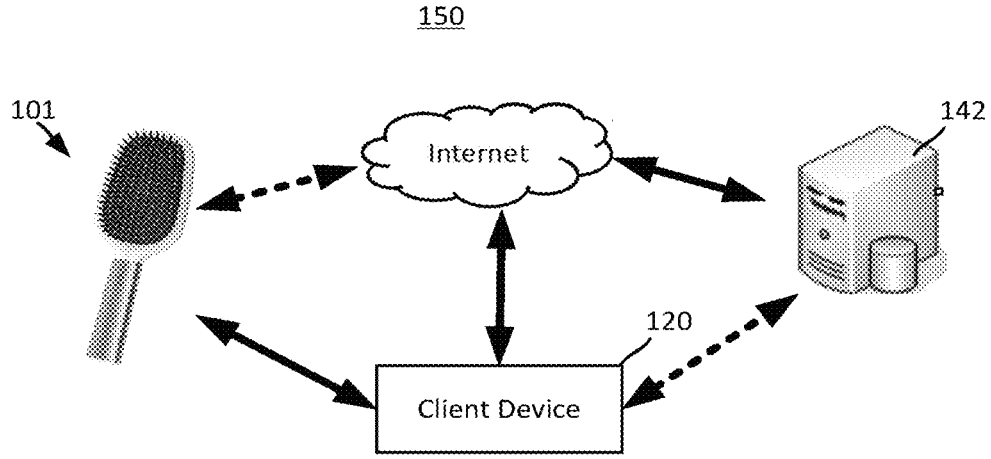
FIG. 4C depicts an alternative system according to an embodiment.

FIG. 4C is a diagram representing an example of a system 150 to promote optimum performance of a hairbrush 101, according to one example. The system 150 includes at least the hairbrush and the client device. Optionally, the system 150 may further include one or more external servers 142 which are implemented as part of a cloud-computing environment and in communication with the system 150 through the Internet. The one or more external servers 142 can store user data, products such as formulations, protocols and routines, tutorials, as well as other $3^{rd}$ party services according to an example.

Figure 5:
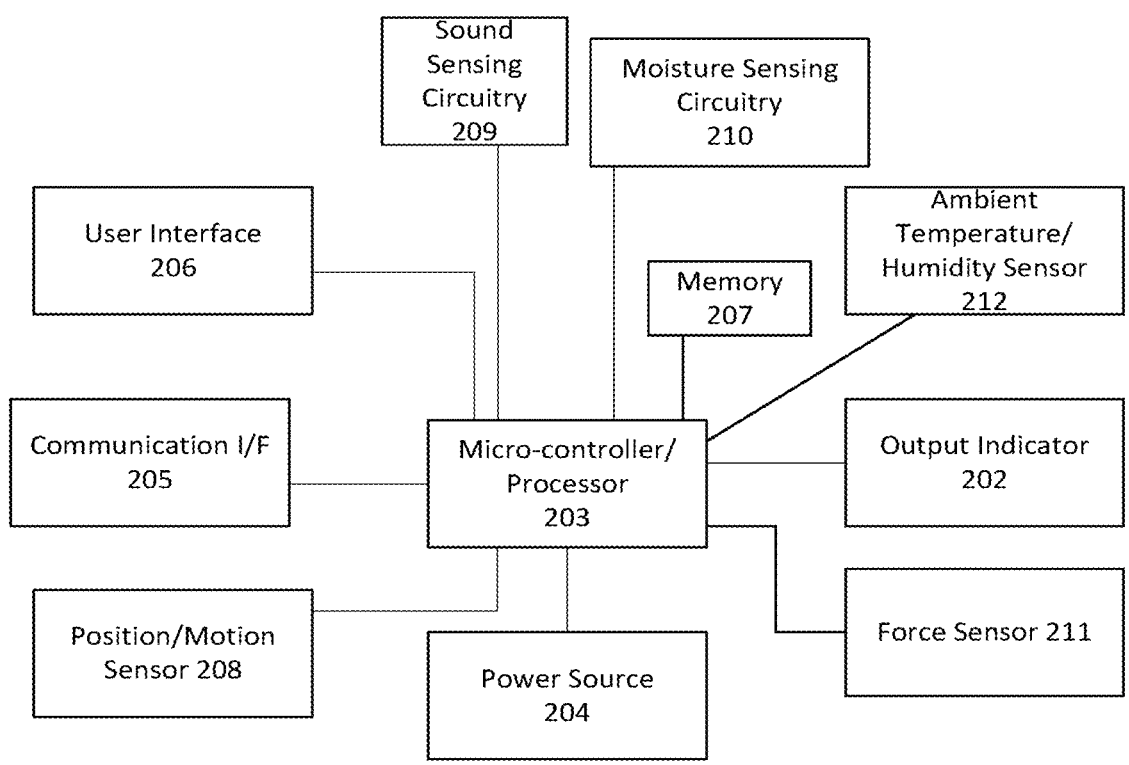
FIG. 5 depicts an electrical/hardware block diagram of the hairbrush according to an embodiment

FIG. 5 shows a diagram of the electrical block diagram of the hardware components of the hairbrush 101. The power from the power source 204 is controlled by the processor 203. It will be appreciated that the electrical block diagram may be modified to adapt to other configurations in accordance with the principles disclosed herein.

In an example, the communication interface (I/F) 205 can include circuitry and hardware for communication with a client device 120. The communication interface 205 may include a network controller such as BCM43342 Wi-Fi, Frequency Modulation, and Bluetooth combo chip from Broadcom, for interfacing with a network. The hardware can be designed for reduced size. For example, the processor 203 may be a CPU as understood in the art. For example, the processor may be an APL0778 from Apple Inc., or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above. The client device may also have similar circuitry and hardware as described above.

In an embodiment, the hairbrush includes a user interface 206, which may be in the form of input buttons on the housing of the tool, or it may be in the form of a contact-sensitive display, such as a capacitive or resistive touch screen display.

In an embodiment, the hairbrush includes output indicator 202 which may be in the form of lights (such as LED lights), an indicator on a touch screen, or an audible output through a speaker.

In an embodiment, the hairbrush includes a memory 207 that stores software for controlling the styling tool, or for storing user data or other information.

In an embodiment, the hairbrush includes a position/motion sensor 208 that can detect an orientation of the styling too as it is being held by the user, and it may also detect movements and motion paths of the styling tool as well. In an embodiment, the position/motion sensor is at least one of or a combination of a geomagnetic sensor and an acceleration sensor. For example, a 3-axis geomagnetic sensor ascertains the direction of geomagnetism, or in other words a geomagnetic vector Vt, given the current orientation of (the housing of) the styling tool housing the 3-axis geomagnetic sensor. A 3-axis acceleration sensor ascertains the direction of gravity, or in other words a gravity vector G, given the current orientation of (the housing of) the styling tool housing the 3-axis acceleration sensor in a still state. The gravity vector G matches the downward vertical direction. The gravity vector G likewise may be decomposed into Xs, Ys, and Zs axis components.

Alternatively, or additionally, a gyroscope may be used which is a sensor that detects angular velocity about the three axes Xs, Zs, and Ys (roll, pitch, and yaw), and is able to detect the rotation of an object. In addition, the geomagnetic sensor is able to ascertain the heading in which the object faces, based on a geomagnetic vector as discussed earlier.

The hairbrush may include sound sensing circuitry 209, which may include a microphone to detect the dryness of the user's hair based on day-to-day energy and spectral sound variation.

The hairbrush may also include moisture sensing circuitry 211. This circuitry may be similar to that described in U.S. application Ser. No. 13/112,533 (US Pub. No. 2012/0291797A1), incorporated herein by reference. Alternatively, the moisture sensing circuitry may rely on a hall-effect sensor which detects changes in a magnetic field, such changes being sensitive to a moisture level.

Additionally, the hairbrush may include conducted pin quills embedded in the hairbrush for detecting if the hair is wet or dry.

The hairbrush may also include a force sensor 211, which may be in the form of a load cell disposed between the head and handle.

The hairbrush may also include an ambient temperature/humidity sensor 212 that detects the local temperature or humidity near the hairbrush.

The client device 120 is configured to collect information about a user and to provide output to the user. The operating system of the client device can have a user interface that is configured to perform multiple functions. In an aspect, the client device can be in communication with a network and enable the user interface access to the Internet as well as Internet of Things (IOT). As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known. In an example, the network can access a server hosting media, protocols, products, personal accounts, stored usage data, and other data related to the appliance, the brushheads, and skin care.

The user interface can display tutorials on how to use the hairbrush. The user interface can create and download protocols for a regimen or routine. The user interface can coach, track usage and compare the tracked usage to the protocol, the regimen, and the routine. The user interface can calculate a score based on the tracked usage. The user interface can store the scores and the tracked usage of the hairbrush in memory of the client device. The user interface can be used to make a purchase of any products related to the hairbrush. For instance, the hairbrush may be used with a combination of styling products or chemical compositions used for treating the user's hair, and the client device can output recommendations on particular styling products or compositions to be used, and which step in the process they are to be used, based on the desired results inputted by the user.

As an initial step, the client device may optionally collects information regarding a user's hair characteristics and usage patterns. The client device may store search results locally or may connect to an external system or server to access the database or search results.

The user may also access tutorials for using the hairbrush to achieve a target look. The tutorials may be in text form, still image form, video form, or audio-only form.

In addition to using the tutorials, the user may connect the client device 120 with the hairbrush over the wireless connection (such as the Bluetooth or Wi-Fi connection) to receive real-time feedback while using the hairbrush, or to record the usage of the hairbrush for later reporting or feedback.

For example, while using the hairbrush, the motion sensor on the hairbrush can output a detection motion of the styling tool as feedback to the client device. The client device is configured to compare the detected motion with predetermined motion data for providing real-time performance results to the user to or to output instructions for the user to make a correction.

The client device can also have a camera function that can be used to provide inputs to the customer profile. For instance, the camera can take images of the user's hair to determine the state of the user's hair based on visual data, or to make further recommendations to the user based on the characteristics of the hair.

The client device is configured to upload data regarding the user to an external system or server (such as a cloud-based system). Such data may include the user profile, amount of use of the hairbrush, or performance results when using the hairbrush. The client device can also provide an option to keep the user data anonymous.

The client device can use the camera function to provide a sharing feature, in which the user can upload photos taken before and/or after the use of the hairbrush. The uploaded photos can be used for receiving feedback from professional hair stylists or other users. In an embodiment, the uploaded photos may be uploaded directly to a social media platform.

Figure 6:
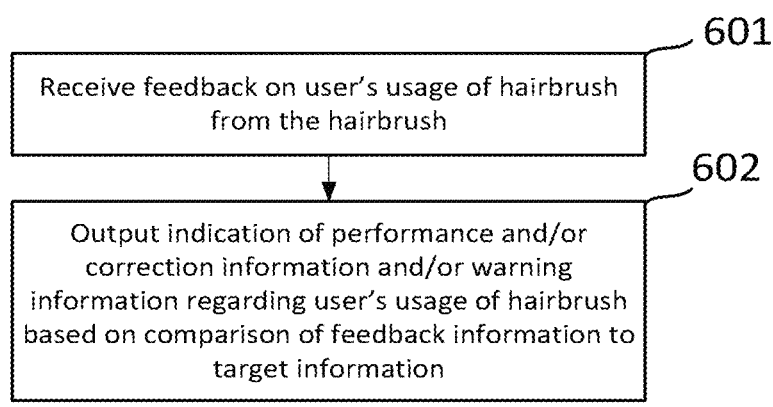
FIG. 6 depicts a method performed by the client device according to an embodiment.

FIG. 6 shows a flowchart of a method performed by the client device based on the above-described features. In step 601, after the user starts using the styling tool, the client device receives feedback on the user's usage of the styling tool from the styling tool (such as feedback from the various sensors incorporated into the hairbrush and described above). In step 605, the client device outputs an indication of the user's performance based on a comparison of the feedback information received from the hairbrush and target information. Alternatively, the client device may output correction information (such as an adjustment of a movement, speed, or force of the hairbrush) based on the feedback information. Alternatively, the client device may output warning information (such as a warning related to a sensed damage or excessive force) to the user based on the feedback information. The output information may differ based on a time period, such that an instant output may be provided based on the recent session or the current day, and also an output based on an aggregated collection of data over time may be outputted. Thus, the output provides session-to-session, day-to-day, or long period assessments of the user's use of the hairbrush and hair health information to coach the user towards better hair health.

Figure 7:
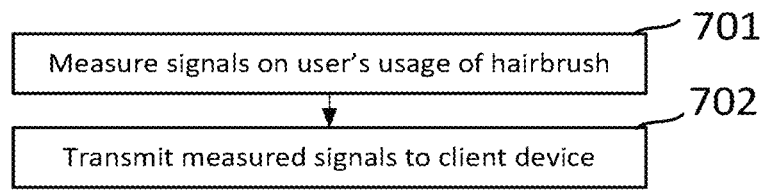
FIG. 7 depicts a method performed by a hairbrush according to an embodiment.

FIG. 7 shows a flowchart of a method performed by a hairbrush according to an embodiment. In step 701, the hairbrush measures one or more signals related to the user's usage of the hairbrush. As discussed above, these signals may be one or more of signals relating to a measurement of sound, acceleration, force, rotation, hair humidity, and ambient temperature and humidity. In step 702, the hairbrush transmits the measured signal to the client device either through wireless or wired transmission.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A system, comprising:
   a hairbrush configured to treat or shape a user's hair and including a motion sensor; and
   a client device configured to communicate with the hairbrush and provide real-time feedback to the user regarding a user's usage of the hairbrush based at least in part on measured data captured by the hairbrush,
   wherein the client device is configured to output assessment information on the user's use of the hairbrush and to output guidance information on a method of using the hairbrush to achieve a target hair health,
   wherein the measured data captured by the hairbrush is a detected motion of the hairbrush detected by the motion sensor, and client device is configured to compare the detected motion with predetermined motion data and output instructions, based on the comparison, for the user to make a correction which includes at least an adjustment of a movement, speed, or force of the hairbrush.

2. The system according to claim 1, wherein the guidance information is image data, video data, or audio data on using the hairbrush.

3. The system according to claim 1, wherein the client device is configured to receive user information regarding physical characteristics of the user and outputs the guidance information based on the received user information.

4. The system according to claim 1, wherein the hairbrush includes circuitry configured to detect one or more of sound, acceleration, force, rotation, hair humidity, and ambient temperature and humidity as the measured data.

5. The system according to claim 1, wherein the outputted assessment information and guidance information is based on measured data received for a single continuous session of the user using the hairbrush.

6. The system according to claim 1, wherein the outputted assessment information is based on measured data received for a predetermined period of time that includes multiple sessions of the user using the hairbrush.

* * * * *